United States Patent

Garr et al.

[11] Patent Number: 5,993,662
[45] Date of Patent: Nov. 30, 1999

[54] METHOD OF PURIFYING AND IDENTIFYING A LARGE MULTIPLICITY OF CHEMICAL REACTION PRODUCTS SIMULTANEOUSLY

[75] Inventors: Cheryl Denise Garr, Woodinville; Lynn Michele Cameron, Snohomish; David R. Schedin, Bainbridge Island; Lauri Marie Schultz, Duvall, all of Wash.

[73] Assignee: Thetagen, Inc., Bothell, Wash.

[21] Appl. No.: 09/143,163

[22] Filed: Aug. 28, 1998

[51] Int. Cl.$^6$ .................................................. B01D 15/08
[52] U.S. Cl. ........................ 210/656; 210/659; 210/198.2; 364/528.03; 364/528.08; 422/70; 422/187; 436/43; 436/161; 702/27
[58] Field of Search .................................. 210/656, 659, 210/198.2; 364/528.03, 528.08; 422/70, 187; 436/43, 161; 702/27

[56] References Cited

U.S. PATENT DOCUMENTS

| | | | |
|---|---|---|---|
| 5,463,564 | 10/1995 | Agrafiotis | 364/500 |
| 5,574,656 | 11/1996 | Agrafiotis | 364/500 |
| 5,684,711 | 11/1997 | Agrafiotis | 364/500 |
| 5,712,171 | 1/1998 | Zambias | 436/518 |
| 5,901,069 | 5/1999 | Agrafiotis | 364/528.03 |

*Primary Examiner*—Ernest G. Therkorn
*Attorney, Agent, or Firm*—Christensen O'Connor; Johnson & Kindness PLLC

[57] ABSTRACT

The invention provides a system utilizing computer databases, high pressure liquid chromatography and mass spectrometry to isolate, purify and identify compounds present in a chemical library of reaction products, especially products of liquid phase (solution) chemical reaction, to produce a purified chemical library with each purified compound tracked to the reaction product from which it originated.

8 Claims, 1 Drawing Sheet

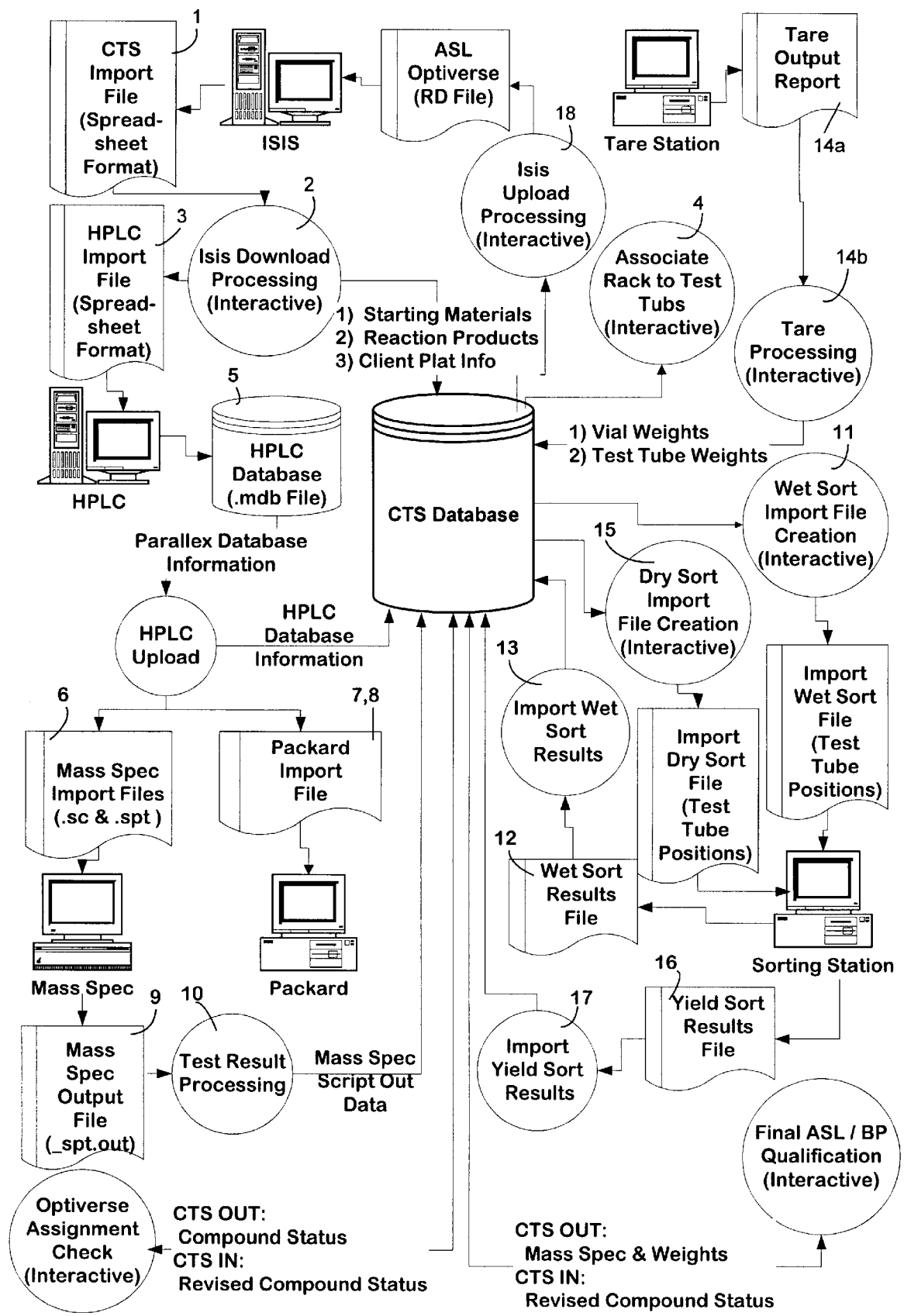

5,993,662

METHOD OF PURIFYING AND IDENTIFYING A LARGE MULTIPLICITY OF CHEMICAL REACTION PRODUCTS SIMULTANEOUSLY

FIELD OF THE INVENTION

The invention provides a method of simultaneously separating chemical compounds from a multiplicity of chemical reaction products using liquid chromatography, and thereafter simultaneously testing and identifying sought-after products in the multiplicity of chemical compounds to produce a large chemical library of purified products from a chemical library of raw reaction products, while maintaining a coding system to relate each identified pure chemical compound to the reaction product from which it originates. The method uses computer software databases to track chemical compounds from reaction product to final purified chemical compound and to identify these.

BACKGROUND OF THE INVENTION

In traditional synthetic and medicinal chemistry, chemists typically synthesize, work-up, purify, and analyze compounds one at a time. However, with the more recent onset of small molecule combinatorial chemical synthesis which provide large chemical libraries, this one-at-a-time method has obvious limitations in requiring large numbers of chemists and equipment leading to high costs and slow turnover. As an alternative, the combinatorial chemist may provide a non-purified reaction product to the client. Of course, this option merely shifts the burden to the client to subsequently carry out whatever purification may be necessary for its purposes, using the same one-at-a-time methods.

With the advent of very large combinatorial chemical libraries, and the need for chemical products in purer form than the raw reaction products produced by liquid phase (solution) synthesis of combinatorial libraries, there exists a need for a method to purify the reaction products, and to identify specific sought-after chemical compounds which are components of the raw reaction products. Moreover, there is a need to separate the identified chemical compound components, each of which may have a different biological activity, so that they may be used separately by a client. There is also a need to relate these identified compounds back to their raw reaction product source, which provides data on how to readily prepare more of each identified compound.

SUMMARY OF THE INVENTION

The invention provides, for the first time, a system for purification and separation of pure or substantially pure chemical components from reaction products making up a large chemical library to produce a chemical library of purified products, by carrying out many steps simultaneously on either each of the plurality of reaction products or its derivatives, or a large plurality of the multiplicity at the same time to allow both savings in time and manpower.

The invention provides a system of simultaneously producing purified compounds from each of a multiplicity of prepared solutions of chemical reaction products that form part of a combinatorial chemical library. The invention further identifies sought-after chemical compound products that are found in each of the multiplicity of prepared chemical reaction products, and allows isolation and separation of these products for subsequent testing for biological activity, or any other purpose.

As explained in more detail below, the invention requires the use of at least one, and preferably several databases, to store information and to allow tracking of a specific chemical compound from the multiplicity of reaction products to the container in which the specific product identified is finally retained. In accordance with the method of the invention, a multiplicity of solutions of reaction products, each in a reaction tube, is identified with a tracking identification code ("TID"), which is also stored in the memory of a digital signal processor (computer). Also stored in the computer database, along with the identifying code for each reaction product, are the sought-after chemical compounds that are expected to be in the reaction product, the reactants used to make the reaction products, and the molecular formula and molecular weight of sought-after product and reactants. The TID also uniquely locates each specific reaction product tube containing a specific reaction product in the array of reaction product tubes.

Either all, or a selected plurality of the multiplicity of reaction tubes containing reaction products, are simultaneously and separately subjected to liquid chromatography. Thus, a series of liquid chromatographs are produced, one for each of the reaction products.

In accordance with the invention, chemical compounds corresponding to each of the identified selected peaks of the liquid chromatographs for each raw reaction product are collected, automatically. In some instances, chemical compounds corresponding to each peak of a chromatograph may be collected, while in others, only chemical compounds corresponding to selected peaks may be collected according to a preselection scheme. These collected chemical compounds are retained in separate purified compound tubes which are coded in a code that relates to the tracking identification number of the reaction product from which it is derived, and the peak of the chromatograph output to which it corresponds. Thus, the method allows tracing of purified isolated compounds back to the reaction tube from which the compound originated using software databases.

In order to identify the chemical compounds in each pure compound tube, a multiplicity of the purified compound tubes are simultaneously sampled into microtiter plates, and each of the samples are separately subjected to mass spectrometric analysis. The output of the mass spectrometer for each of the individual compounds is compared with a database containing the mass for the compounds expected to be present in the particular purified compound tube (and thence the original reaction tube) from which the sample originated. In this manner, the chemical compound in the purified compound tubes can be identified and prioritized.

After mass spectrometry and identification of compounds, compounds are sorted (into sought-after compounds, by-products, residual reactants) and solvent is removed from the purified sought-after compounds to produce dried, purified compound that may be stored. Otherwise, the purified compounds may be used to prepare a purified chemical library. In that instance, the mass of purified chemical compound in each tube is determined, and the tubes are arranged by descending order of contained mass, in an array. A predetermined quantity of solvent is added to each of the multiplicity of tubes, in an amount sufficient to produce equal concentrations in each tube. Samples are taken from each of the tubes and transferred to microtiter plates. The wells of each of the plates are selected by row and column to correspond with the location of the purified compound tubes, so that contents of any well of the microtiter plate can readily be identified. The microtiter plate, after solvent evaporation, provides a purified chemical library of identified chemical products for each well of the plate.

The invention provides a significant advantage in that it allows for the purification and separation of pure or substantially pure chemical compounds from a multiplicity of reaction products, in a cost-effective and less time-consuming method than the one-to-one method of the past. The invention uses tracking software that allows the operator to maintain a record of the contents of any one of the multiplicity of reaction tubes through the process, so that the ultimate purified product provided on a microtiter plate can be related back through databases to the original reaction tube from which the product originated and it can be correlated with the multiplicity of subsequent chromatograph plates from the reaction product.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawing, wherein the one FIGURE is a schematic diagram of the system of the invention showing database relationships.

DETAILED DESCRIPTION OF THE PREFERRED EMBODIMENTS

The invention provides a method or system of simultaneously purifying a multiplicity of raw reaction products that form a large combinatorial chemical library, and produces separate substantially pure chemical compound(s) from each of the multiplicity of reaction products, while relating each pure chemical compound by code to the original reaction product from which it is derived.

In order to achieve the benefits of the invention, the system requires the use of at least one digital signal processor (computer) with a memory for storing a database of information relating to each raw reaction product (and a tracking identification code for that product), expected chemical compounds present in the raw reaction product, mass spectrometry data relating to each of the expected chemical compounds, molecular weights and molecular formulae of the compounds, reactants for making the reaction product, and reaction pathway. Of course, more than one computer and more than one database, each containing some of the data and able to interact with each other, may also be used.

The term "multiplicity" as used in the specification and claims, when referring to reaction products and purified chemical compounds means a large number of such items, for example, not less than 48 and preferably greater than 288. Thus, the invention is intended for application to large combinatorial chemical libraries which contain large numbers of reaction products in unpurified or less-pure-than-desirable form. For example, such reaction products may be produced by solution phase chemistry, as described in our co-pending patent application entitled "Methods for Production of Large Catalogued Chemical Libraries," U.S. Ser. No. 08/371,543, filed Jan. 11, 1995, hereby fully incorporated by reference. Of course, the combinatorial chemical library of raw reaction product may also be prepared by other techniques.

There are clearly a variety of ways in which information can be stored and retrieved in a system for tracking the purification of raw reaction products into purified chemical coripounds, in accordance with the invention, which will become clear to a person of ordinary skill in the art upon reading this disclosure. The system described in the specification and the FIGURE is a nonlimiting example of a preferred system.

In accordance with the invention, the starting point raw combinatorial chemical library of reaction products is arranged in an array, with each reaction tube containing a reaction product and each reaction tube and product identified by a unique code, such as a bar code, which is optically readable or in a microtiter plate format with identifiers for each well and plate. The code is also stored in the memory of a digital signal processor on a database. An example of such a database is the ISIS database which is available from MDL Information Systems of California. For each reaction product, the ISIS database has a reaction product file that includes such information as the molecular formula and molecular weight of the sought-after product; reaction series identification; substrate and reagent identification; molecular weight and molecular formula; and the bar code of the microtiter plate (or tube rack) on which the product is found, along with the specific well (or tube) location of the reaction product on the plate (or tube rack). The same or another file contains information regarding the starting materials used to prepare the reaction product, such as molecular weight and molecular formula. Usually, the sought-after product (or "ASL") should comprise the largest proportion of the material in the reaction product tube, if reaction proceeded according to design. Also present in the reaction product tube are by-products, and residual unreacted chemicals. The database may include a listing of expected by-products, in addition to the reagents or reactants used to prepare the reaction product.

For each reaction product tube, the database may also include the tare mass of the purified compound tubes to which its components will later be transferred, as described below. This information may be used to calculate yield of sought-after product, based on either total reaction product in the tube, or mass of reactants combined to produce the reaction product.

Referring to the FIGURE, ISIS creates an EXCEL (product of Microsoft Corporation of Redmond, Wash.) file which is uploaded into the compound tracking system (CTS) database in step 1. The CTS database in turn creates a second EXCEL file 2 to download information into the computer-assisted high-pressure liquid chromatography (HPLC) apparatus in step 3, such as for example one or more of the PARALLEX high pressure liquid chromatography instrument sold by Biotage, a division of DYAX of Charlottesville, Va.

Information regarding a coded rack and its wells (or a rack and test tubes) is also input to the CTS database in step 4. This rack and its test tubes, arranged in an array, will be used to contain purified chemical compounds, as explained below. Preferably, the containers or test tubes are pre-weighed so that the weight of the individual test tube can also be input into the CTS database.

The CTS database then generates a tracking identification number ("TID"), which is uniquely associated with each of the multiplicity of test tubes arrayed on the rack.

In accordance with a preferred embodiment of the invention, the separation and purification of individual chemical compounds from the raw reaction products in the reaction tubes proceeds through the use of liquid chromatography. As a first step, if the reaction products are not in solution, then an appropriate solvent is added to the reaction tube to produce a solution of the reaction products. This is a necessary precursor to liquid chromatography.

The multiplicity of reaction tubes filled with solutions of reaction products are at the beginning arrayed on a rack or other holder in an order tracked by the CTS database. Thus, operating personnel can determine the contents, and possible products and by-products of each reaction product tube by reference to tube location in the array (and the code of the rack in which the array is set up) from data stored on the CTS database.

In accordance with the invention, a multiplicity of the array of reaction product solutions are simultaneously and separately charged to liquid chromatography so that each produces a chromatograph that includes a series of peaks. Under ideal conditions, the largest peak will correspond to the sought-after product in each reaction tube. However, under certain circumstances, the largest peak may in fact correspond to unreacted reactants, or a by-product. Moreover, certain chemicals may produce a larger peak than others, even though they may be present in smaller quantity. The invention provides a technique for separating out the sought-after products from the by-products and reactants. This technique includes selecting predetermined threshold peak height, area and slope parameters and rejecting those not meeting this criterion.

The term "substantially pure chemical compound", as used in this specification and claims, refers to a chemical compound as a high degree of purity relative to the raw rceaction products from which the chemical compounds are :derived. One of skill in the art will readily recognize that any chemical compound, even after purification, may contain a "contaminant" to a greater or lesser degree. Accordingly, although the purified chemical compounds have been "purified", absolute purity may not be necessarily be obtained, without significant sacrifice of yield.

The liquid chromatography technique allows separation of individual compounds in the reaction product automatically, for a multiplicity of reaction products simultaneously. Thus, an entire chemical library, or a large proportion of a chemical library can be virtually simultaneously treated by liquid chromatography to separate each reaction product into its constituent individual pure (or substantially pure) chemical compounds. In accordance with the invention, each of the individual chemical compounds, are contained in separate purified compound tubes, which are identified by location in an array, as explained herein and which are coded. The codification of these tubes preferably provides a ready correspondence with the code of the original reaction product tube from which the purified chemical compounds were separated by liquid chromatography. Thus, the code may be the TID of the reaction product combined with the peak number to which the compound corresponds.

Preferably the HPLC's database 5 associates the purified compound tube array rack data with the data from the ISIS database so that each purified compound is associated with a specific peak obtained from a chromatograph of a specific one of the multiplicity of reaction products that have undergone liquid chromatography separation. In addition, the HPLC's database contains the peaks obtained for each of the purified compounds, the volume of the compound, its retention time in the system, and the solvent utilized. This information is uploaded from the HPLC's database to the CTS database.

In accordance with the invention, a large number of the multiplicity of the arrayed purified compound tubes are simultaneously sampled and each sample is separately charged to a mass spectrometer where each sample is analyzed. The sample array conforms to the purified product tube array so that the product in each well of the microtiter sample plate is known and tracked. A useful high throughput mass spectrometer is Sciex Model API-150MCA, and preferably several of these are used simultaneously to increase overall rate of testing. The output for each compound from the mass spectrometer is compared with the mass data in the database corresponding to the sought-after compound in the reaction product from which the purified compound originated, and the chemical reagents that produced the reaction product. Based on this comparison, each of the samples can be identified to correspond to either a sought-after product, or a reactant, or a by-product.

After such classification, the array comprising the multiplicity of purified compound tubes may be sorted and arrayed in a different order, to reflect products and by-products. Those tubes containing residual reactants may be discarded. Moreover, in certain instances, the by-products might also be discarded, if it is not expected that they would be biologically or otherwise commercially useful. Notwithstanding, since each purified compound tube is identified by location in the array, one can readily identify its contents by entering this data into the computer, and reviewing the database.

In the specific embodiment described in the FIGURE, the HPLC's database also creates three separate files although other techniques may also be used. In this instance, the three files include a first import file 6, and two separate mass spectrometry input files 7, 8. The first import file 6 contains instructions to select samples of purified compounds to create a microtiter plate of samples for mass spectrometry analysis. The file establishes a plate bar code identification.

The mass spectrometry files 7, 8 instruct the mass spectrometer (such as for example one or more of those sold by Packard) where the specific samples are located, and contain compound tracking identification number, plate bar code identification numb(r (established by the first import file), peak and product well location; molecular weight and molecular formula of each compound; substrate identification, molecular weight and formula; and reagent identification, molecular weight and formula.

A multiplicity of samples are subject to mass spectrometry analysis, and the mass spectrometer output file 9 contains such information as tracking identification number, molecular weight, molecular formula, and result (whether a sought-after product has been found); base peak identification (molecular weight); area under the mass spectrometer output curves; substrate identification, formula and weight, and whether it was found; and reactant identification, formula and weight, and whether it was found. Ideally, the spectrometers can be run continuously overnight, as with the HPLC.

In processing the test results (in step 10) of the mass spectrometer, certain predetermined criteria may be set. For example, mass spectrometer peaks may be examined and, based on peak height and other characteristics such as area under the peak, a decision can be made whether to keep or discard the corresponding purified product. The test results are uploaded to the CTS database after processing.

At this point, the purified compounds are in tubes with identified, stored locations on identified racks. The purified compounds are in solution form or "wet." In accordance with the invention, the wet sort import file creation step 11 is preferably interactive. Operators are able to view the data, and may alter these manually, or set automatic criteria. During wet sorting on the sorting station such as the Bohdan sorting stations, provided by Bohdan Instrument Company, all sought after products are separated from those tubes that contain by-products, and unreacted reagents. The sought after product tubes are arranged in identified racks in rows and columns, while keeping track of the location by row and column of each specific tube in the array of the rack. The wet sort results file 12 containing this information is then uploaded to the CTS database through import file 13. Accordingly, at this point, the location of each purified compound on the rack is updated in the CTS database, including whether the tube contains a sought-after compound, an unreacted reagent, or a by-product.

The multiplicity of solutions of purified compounds are then subjected to solvent removal, preferably by evaporation, to produce dried product. The individual product tubes are then weighed on a tare station producing a tare output which is subject to processing for subtracting the mass of the specific empty test tube previously input to the CTS database (step 14). As a result, a dry yield in grams of each of the purified compounds is determined.

The dry yield results are then downloaded to the sorting station through a dry sort import file 15 from the CTS database. The sorting station rearranges the tubes in descending order of the mass of their respective contents, while keeping track of the change in location and ultimate location of each purified compound test tube in the array. The new dry sort file 16 is uploaded through import file 17 to the CTS database, to update the database with the new location for each purified compound tube. The CTS database, as updated, may then be used to upload information to the ISIS database in step 18, to update the ISIS database with compound location and status (whether sought-after compound or by-product).

In accordance with the invention, the dry yield may be used to calculate the amount of solvent to be added to each of the purified compound tubes to produce equimolar concentration (or equal concentrations in grams per liter) for each compound in the array. Once calculated, using the CTS database, an instrument may be programmed to automatically dispense the calculated amount of solvent into each specific purified compound tube to produce the desired equal concentrations.

Samples may be taken from each of the multiplicity of purified compound solutions of equal concentration, and dispensed into microtiter plates, while maintaining the row and column location for each compound in correspondence with the tubes on the rack. The solutions in the microtiter plate may be evaporated, to produce a microtiter plate containing dried purified compounds arranged in an array in which the location of each compound is coded to its identification. In order to prepare a purified chemical library for a client, a small predetermined sample is removed from each of the multiplicity of tubes simultaneously, and titered into a multi-well microtiter plate. Thus, the invention provides a comprehensive method for purifying a raw chemical library of reaction products into chemical libraries of high purity, suitable for a variety of purposes.

Thus, for instance, the chemical compound in the second row of the array, and in the third column, may be determined by reference to the same array in the computer database, which will identify the chemical compound present.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A system of simultaneously purifying a multiplicity of solutions of chemical reaction products using liquid chromatography and identifying sought-after products using mass spectrometry, while tracking chemicals present in individual reaction products using computer memory, the system comprising:

(a) selecting an array of a multiplicity of reaction tubes, each tube containing a solution, of a chemical reaction product, each tube coded with an identifying code, the code stored in a memory of a digital signal processor to identify the chemical reaction product;

(b) subjecting at least some of the multiplicity of reaction products separately and simultaneously to liquid chromatography to produce a chromatograph for each, the chromatograph comprising a series of peaks representing individual chemical compounds contained in each reaction product;

(c) automatically collecting individual chemical compounds corresponding to peaks of the chromatographs of the plurality of the reaction products into an array of separate purified chemical compound tubes and coding with a second code, traceable to the identifying code of the reaction product from which the purified compound is obtained, the second code stored in a computer database;

(d) simultaneously sampling a multiplicity of the purified compound tubes while maintaining tracking correspondence between each sample and each purified compound tube and subjecting each of the samples separately to mass spectrometric analysis; and (e) comparing output from the mass spectrometric analysis for each sample with data identifying known compounds expected to be present in the reaction products, the data stored in a database of a digital signal processor, to identify samples as containing particular chemical compounds.

2. The system of claim 1, further comprising removing solvent from each of the purified compound tubes to provide a chemical library of dried purified compounds, each identified by its location in an array and tracking date in a database.

3. The system of claim 2, further comprising determining the mass of the dried purified compound produced in each of the purified compound tubes.

4. The system of claim 3, further comprising sorting the purified compound tubes to separate tubes containing sought-after products from other tubes, the sorting based on comparing mass spectrometric analysis output data with data stored in a digital signal processor memory identifying each sought-after compound by molecular weight and molecular formula.

5. The system of claim 4, further comprising evaporating solvent from each of the purified compound tubes, determining a mass of each purified compound, and arranging the purified compound tubes in order of descending mass of purified compound contained therein.

6. The system of claim 5, further comprising determining, by reference to a computer database storing mass and molecular weight of each purified compound, an amount of solvent to be added to each purified compound tube to produce solutions of equal concentration in each tube of the array of purified compound tubes.

7. The system of claim 6, further comprising sampling each of the purified compound containers; placing each sample into a separate well of a microtiter plate corresponding to a location of a purified sample in the array, while tracking and maintaining a record of each well location on the plate and chemical compound inserted into each well;

and drying samples in the wells to produce a dried chemical library of purified compounds on the microtiter plate.

8. A system of purifying a multiplicity of solutions of chemical reaction products using liquid chromatography and identifying sought-after products using mass spectrometry, while tracking chemicals present in individual reaction products using databases, to prepare a purified chemical library, the system comprising:

(a) selecting an array of a multiplicity of chemical reaction products, each reaction product of the array coded with an identifying code, the code stored in a memory of a computer to identify the chemical reaction product by location in the array;

(b) subjecting a multiplicity of the multiplicity of reaction products separately to liquid chromatography to produce a chromatograph for each of the reaction products so subjected, each chromatograph comprising peaks representing individual chemical compounds contained in a particular reaction product;

(c) automatically collecting chemical solution corresponding to peaks of the chromatographs into an array of purified chemical compound tubes, the tubes coded with a second code traceable to the identifying code of the chemical reaction product from which the purified chemical compound originates and the peak of the chromatograph to which said purified compound corresponds, the second code stored in a computer database;

(d) sampling a multiplicity of the purified compound tubes, while maintaining tracking correspondence between each sample and each purified compound tube, and subjecting each of the samples separately to mass spectrometry analysis;

(e) comparing output from the mass spectrometry analysis for each sample with data identifying known compounds expected to be present in the reaction product from which a particular purified compound originates, to identify samples as containing particular chemical compounds;

(f) sorting identified sought-after compounds of the purified compounds into an array;

(g) evaporating solvent from the sorted array of compounds, to produce and array of dried compounds;

(h) determining the mass of each sorted dried compound, and rearranging the compounds in accordance with a pre-selected criterion, while maintaining tracking correspondence between each of the dried purified compounds and the reaction product from which it originates;

(i) adding a predetermined amount of solvent to the dried purified compounds to produce an array of equal concentration solutions of purified compounds;

(j) sampling the solutions of purified compounds, and dispensing samples into microtiter plates, while maintaining tracking correspondence between purified sample containers and microtiter wells, to produce a chemical library of dried purified compounds, each compound identified by its location in the an array of wells of the microtiter plate and tracking data in a database.

* * * * *